(12) United States Patent
Choi et al.

(10) Patent No.: US 12,109,030 B2
(45) Date of Patent: Oct. 8, 2024

(54) BIO SENSOR HAVING PILLER-TYPED ELECTRODE STRUCTURE COATED NON-CONDUCTIVE MATERIAL

(71) Applicant: UIF (University Industry Foundation), Yonsei University, Seoul (KR)

(72) Inventors: Heon Jin Choi, Seoul (KR); Jae Suk Sung, Suwon-si (KR)

(73) Assignee: UIF (UNIVERSITY INDUSTRY FOUNDATION), YONSEI UNIVERSITY, Seoul (KR)

( * ) Notice: Subject to any disclaimer, the term of this patent is extended or adjusted under 35 U.S.C. 154(b) by 692 days.

(21) Appl. No.: 17/132,635

(22) Filed: Dec. 23, 2020

(65) Prior Publication Data

US 2021/0196178 A1 Jul. 1, 2021

(30) Foreign Application Priority Data

Dec. 30, 2019 (KR) ........................ 10-2019-0177776

(51) Int. Cl.
*A61B 5/263* (2021.01)
*A61B 5/25* (2021.01)
*A61N 1/04* (2006.01)

(52) U.S. Cl.
CPC ...... *A61B 5/263* (2021.01); *A61B 2562/0209* (2013.01); *A61B 2562/046* (2013.01); *A61N 1/0476* (2013.01)

(58) Field of Classification Search
CPC ............ A61B 5/263; A61B 2562/0209; A61B 2562/046; A61B 5/02438; A61B 5/282; A61B 5/0536; A61B 5/6831; A61B 2562/164; A61N 1/0476; A61N 1/0492
See application file for complete search history.

(56) References Cited

U.S. PATENT DOCUMENTS

| | | | |
|---|---|---|---|
| 11,019,734 B1* | 5/2021 | Davis | H10K 85/221 |
| 2018/0177417 A1* | 6/2018 | Kipke | A61B 5/24 |
| 2021/0310979 A1* | 10/2021 | Gandolfo | G01N 33/4836 |

FOREIGN PATENT DOCUMENTS

| | | |
|---|---|---|
| KR | 10-2012-0055227 | 5/2012 |
| KR | 10-2017-0122592 | 11/2017 |

OTHER PUBLICATIONS

KIPO, Office Action of KR 10-2019-0177776 dated May 20, 2021.

* cited by examiner

*Primary Examiner* — Adam Z Minchella
(74) *Attorney, Agent, or Firm* — LEX IP MEISTER, PLLC

(57) ABSTRACT

Disclosed herein is a biosensor capable of receiving bio-electric stimulation or bio-signals. The biosensor has a pillar-type electrode structure that is coated with a non-conductive material. The biosensor includes an electrode substrate, and an electrode structure having a plurality of pillar electrodes protruding on the substrate. The pillar-type electrode structure is coated with the non-conductive material in at least one of: a first coating structure in which at least one or more of the plurality of pillar electrodes are coated with the non-conductive material and at least a portion of a side surface of each of the coated pillar electrodes is coated with the non-conductive material; and a second coating structure in which at least one of a top surface of the substrate and bottom surfaces of the at least one or more of the pillar electrodes are coated with the non-conductive material.

14 Claims, 14 Drawing Sheets

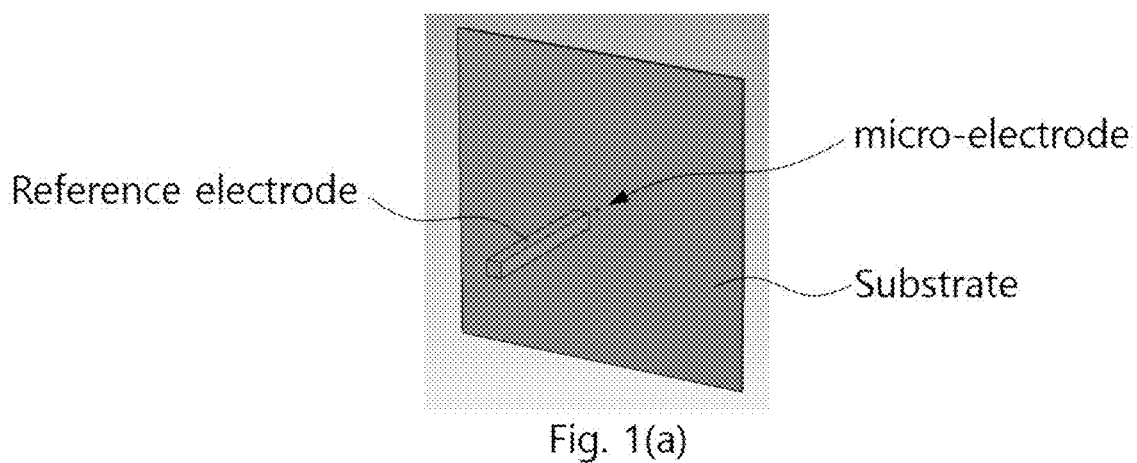
Fig. 1(a)
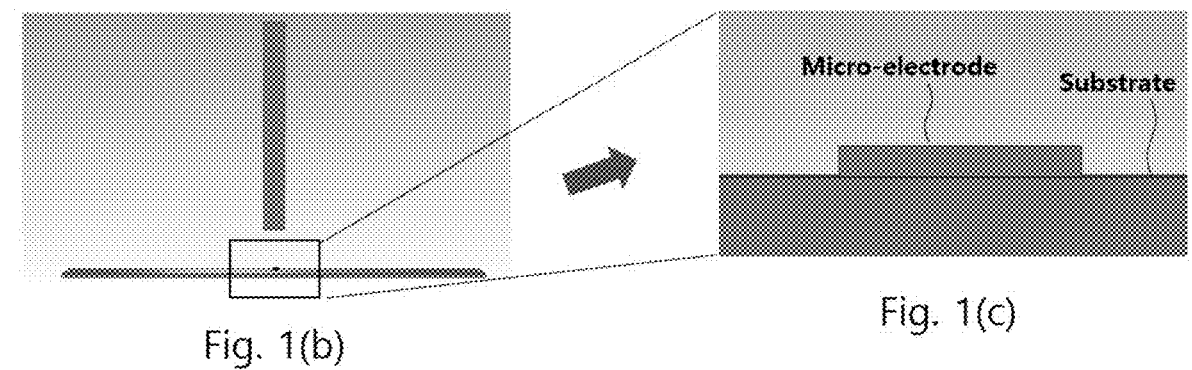
Fig. 1(b)
Fig. 1(c)

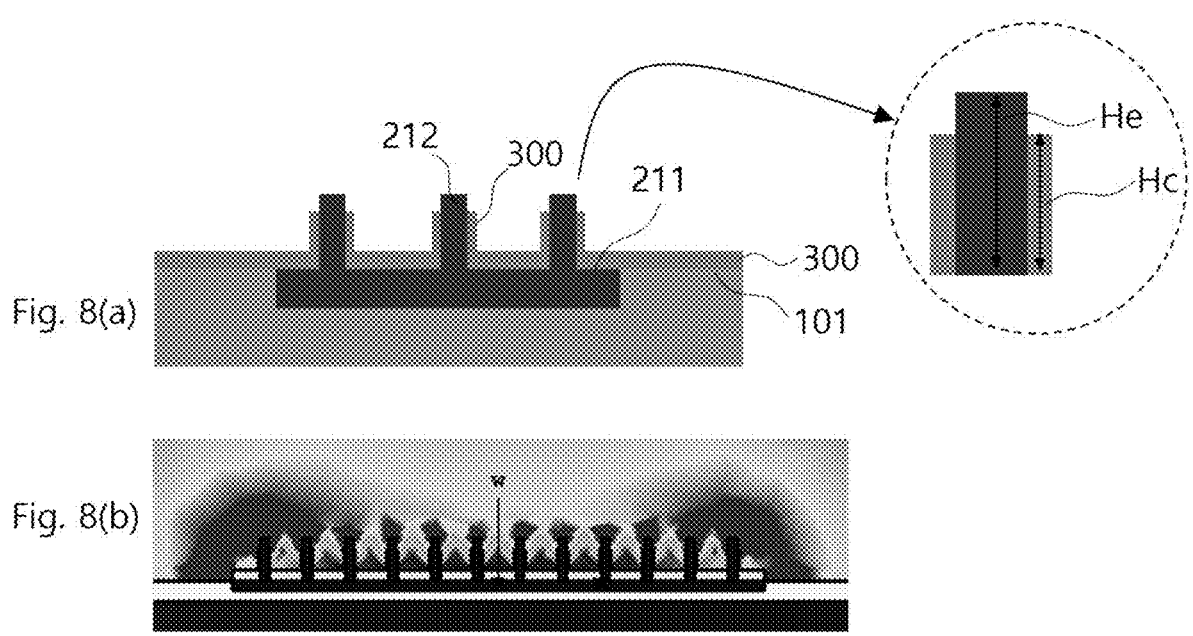

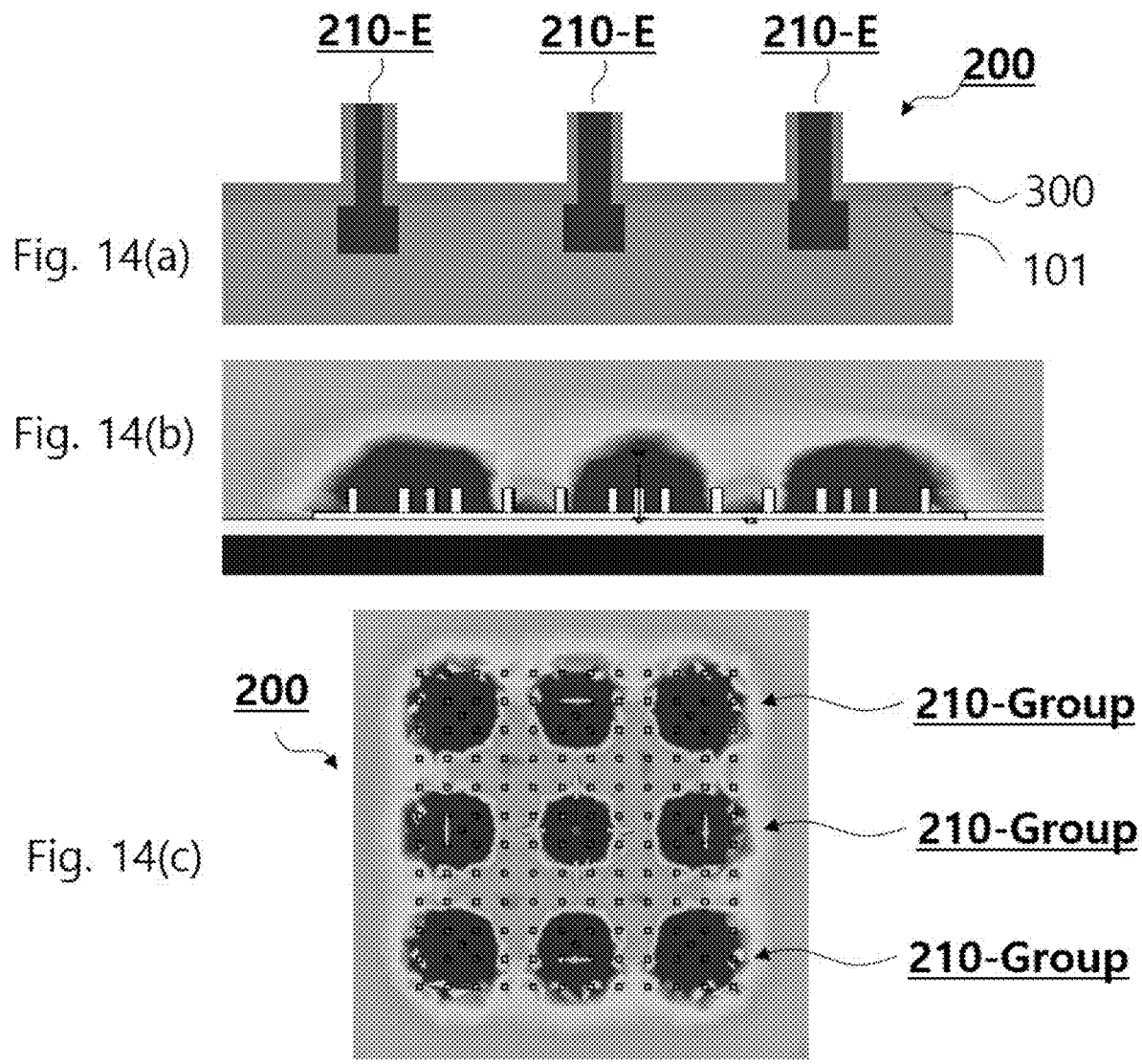

BIO SENSOR HAVING PILLER-TYPED ELECTRODE STRUCTURE COATED NON-CONDUCTIVE MATERIAL

CROSS-REFERENCE TO RELATED APPLICATION

This application claims the benefit of Korean Patent Application No. 10-2019-0177776 filed on Dec. 30, 2019, which is hereby incorporated by reference herein in its entirety.

BACKGROUND

1. Technical Field

The present invention relates generally to a biosensor having a pillar-type electrode structure. More specifically, the present invention relates to a biosensor having a pillar-type electrode structure coated with a non-conductive material.

2. Description of the Related Art

Recently, research has been conducted to obtain new characteristics by forming an electric field in a microscopic area, such as a cell, and stimulating the cell using this field energy, thereby changing the cell itself or changing the physical properties of a nearby area.

Furthermore, there has been actively conducted research into the field of nerve-related problem treatment, such as the radiation of such energy onto the nerves of the human body to apply stimulation and reduce pain.

According to a general method of providing energy, an electric field is formed by applying a predetermined voltage between two electrodes, and the physical properties of a cell are changed or stimulation is applied using the formed electric field energy.

In this case, in order to obtain a strong electric field, a high voltage is generally applied between the electrodes. Accordingly, a problem arises in that a large amount of electric power is required to obtain high energy.

In addition, since field energy such as an electric field has the characteristic of spreading over a wide range, it is considerably difficult to radiate energy to only a specific desired area, especially a small area.

PRIOR ART DOCUMENT

Patent Document

Korean Patent No. 10-1613578 (published on Mar. 12, 2016)

SUMMARY

A biosensor having a pillar-type electrode structure coated with a non-conductive material according to the present invention has the following objects:

First, the present invention is intended to propose a structure that concentrates energy formed between microelectrodes.

Second, the present invention is intended to control the size and area of concentrated energy by forming microelectrodes in a pillar structure and changing the pillar structure and shape.

Third, the present invention is intended to control the size and area of concentrated energy by coating microelectrodes and a substrate with a non-conductive material.

Fourth, the present invention is intended to control the size and area of concentrated energy by selecting one or more electrodes to which a voltage is applied.

The objects of the present invention are not limited to those mentioned above, and other objects that are not mentioned will be clearly understood by those skilled in the art from the following description.

According to an aspect of the present invention, there is provided a biosensor capable of receiving bioelectric stimulation or bio-signals, the biosensor having a pillar-type electrode structure coated with a non-conductive material, the biosensor including: an electrode substrate; and an electrode structure having a plurality of pillar electrodes protruding on the substrate; wherein the pillar-type electrode structure is coated with the non-conductive material in at least one of: a first coating structure in which at least one or more of the plurality of pillar electrodes are coated with the non-conductive material and at least a portion of a side surface of each of the coated pillar electrodes is coated with the non-conductive material; and a second coating structure in which at least one of a top surface of the substrate and bottom surfaces of the at least one or more of the pillar electrodes are coated with the non-conductive material.

In the present invention, the plurality of pillar electrodes may have the same electrode height.

In the present invention, the plurality of pillar electrodes may be provided such that the electrode heights thereof decrease or increase toward the inside of the electrode structure.

In the present invention, in the first coating structure, a coating height on the side surfaces of the pillar electrodes may be the same as the electrode height.

In the present invention, in the first coating structure, a coating height on the side surfaces of the pillar electrodes may be lower than the electrode height.

In the present invention, in the first coating structure, coating heights on the side surfaces of the pillar electrodes may gradually decrease or increase toward the inside of the plurality of pillar electrodes.

In the present invention, in the first coating structure, the pillar electrodes to be coated may be pillar electrodes disposed on the outermost sides of the electrode structure and the outer side surfaces of the pillar electrodes disposed on the outermost sides of the electrode structure may be coated with the non-conductive material.

In the present invention, the electrode structure may be provided such that a plurality of pillar electrode groups each including adjacent pillar electrodes are spaced apart from each other.

In the present invention, a voltage may be applied to predetermined one or more of the plurality of pillar electrodes of the electrode structure.

In the present invention, the pillar electrodes to which the voltage is applied may be spaced apart from each other.

In the present invention, at least one of the bottom and side surfaces of each of the pillar electrodes to which the voltage is applied may be coated with the non-conductive material.

In the present invention, the electrode structure may be provided such that a plurality of pillar electrode groups each including adjacent pillar electrodes are spaced apart from each other; and a voltage may be applied to pillar electrodes belonging to predetermined one or more of the pillar electrode groups.

In the present invention, the bottom and side surfaces of each of the pillar electrodes to which the voltage is applied may be coated with the non-conductive material.

BRIEF DESCRIPTION OF THE DRAWINGS

The above and other objects, features, and advantages of the present invention will be more clearly understood from the following detailed description taken in conjunction with the accompanying drawings, in which:

FIGS. 1(a) and 1(b) are schematic diagrams of a structure for forming energy between electrodes, and FIG. 1(c) is a partially enlarged view of FIG. 1(b);

FIG. 8(a) shows an embodiment in which the top surface of a substrate and the bottom and side surfaces of pillar electrodes are coated with a non-conductive material and the coating height of the side surfaces of the pillar electrodes is lower than the height of the pillar electrodes, and FIG. 8(b) shows the electric field distribution of the embodiment shown in FIG. 8(a);

FIG. 14(a) shows an embodiment in which an electrode structure is provided such that a plurality of pillar electrode groups each including adjacent pillar electrodes are spaced apart from each other and electricity is supplied to pillar electrodes belonging to predetermined pillar electrode groups, FIG. 14(b) shows the electric field distribution of the embodiment shown in FIG. 14(a), and FIG. 14(c) shows a state in which the plurality of pillar electrode groups are provided to be spaced apart from each other.

DETAILED DESCRIPTION

Figure 2A:
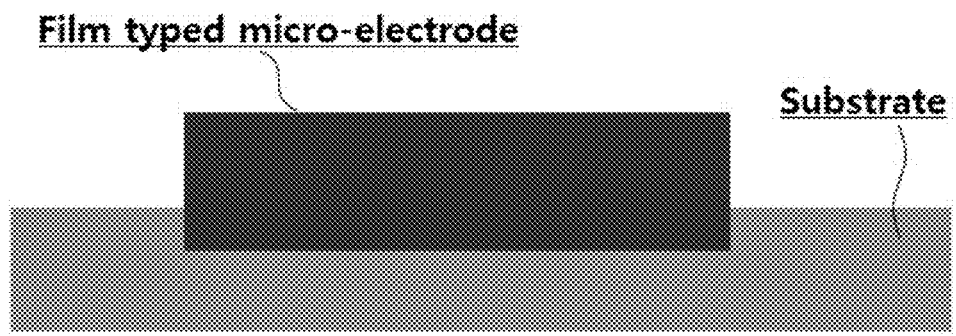
FIGS. 2(a), 2(b) and 2(c) show a sectional structure, an electric field distribution, and electric field directions in the case where the microelectrode of a substrate transmitting energy is implemented in the form of a film having a predetermined thickness.

Embodiments of the present invention will be described with reference to the accompanying drawings so that those of ordinary skill in the art to which the present invention pertains can easily practice the present invention. As can be easily understood by those of ordinary skill in the art to which the present invention pertains, the embodiments to be described later may be modified in various forms without departing from the concept and scope of the present invention. The same or similar portions are denoted by the same reference numerals throughout the drawings as much as possible.

The technical terms used herein are intended merely to refer to specific embodiments, but are not intended to limit the invention. In this case, the singular forms used herein also include plural forms unless the phrases clearly indicate the opposite.

The meaning of the term "including" specifies a specific feature, region, integer, step, operation, element, and/or component, but does not exclude the presence or addition of another specific feature, region, integer, step, operation, element, component and/or a group thereof.

All the terms including technical or scientific terms used herein have the same meanings as commonly understood by those of ordinary skill in the art to which the present invention pertains. The terms defined in the dictionaries are further interpreted as having meanings consistent with the related technical documents and the presently disclosed content, and are not interpreted as having ideal or excessively formal meanings unless defined as such.

The present invention will be described below with reference to the accompanying drawings. For reference, the drawings may be partially exaggerated to describe the features of the present invention. In this case, it is preferable to perform interpretation in light of the overall purpose of the present specification.

The present invention relates to a new concept-based energy concentration system capable of concentrating energy such as an electric field, a magnetic field, current density, etc. by utilizing a pillar-type micro/nano-structure.

The present invention proposes a new method capable of concentrating energy formed between electrodes and controlling the amount and area of energy by forming a pillar-type microelectrode structure on an electrode surface and adjusting the form factors of the pillar-type microelectrode structure.

FIGS. 1(a) and 1(b) are schematic diagrams of a structure for forming energy between electrodes, and FIG. 1(c) is a partially enlarged view of FIG. 1(b).

Referring to FIG. 1, a microelectrode is formed on a substrate 200. When a predetermined voltage is applied between the microelectrode and a reference electrode, electric field energy is formed.

In general, in order to form high electric field energy, a high voltage needs to be applied between both ends of the electrode. The energy distribution to be formed is determined according to the position of the electrode.

In the present invention, there is proposed a new method of forming high energy by controlling and concentrating an energy distribution even when a low voltage is formed.

Figure 2B:
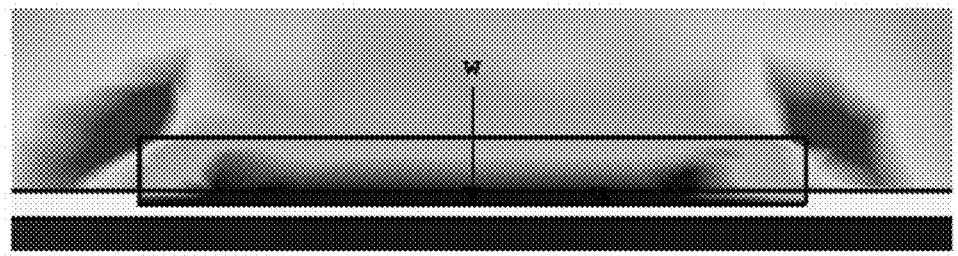
Figure 2C:
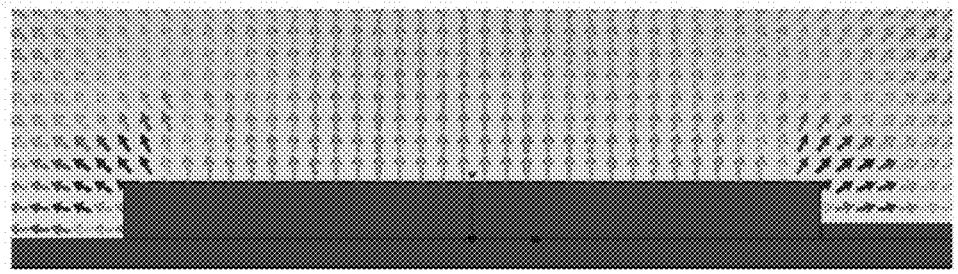

FIGS. 2(a), 2(b) and 2(c) show a sectional structure, an electric field distribution, and electric field directions in the case where the microelectrode of a substrate transmitting energy is implemented in the form of a film having a predetermined thickness.

FIG. 2 shows sectional views of an electric field distribution and direction simulation values formed around the electrode when the microelectrode of the substrate transmitting energy is implemented in the form of a film having a predetermined thickness.

It can be seen that if a voltage is applied in a general electrode shape in the device of FIG. 1, a weak electric field is formed in the flat portion of the electrode and electric fields are concentrated in the edges of the electrode instead.

This phenomenon appears even when electric field direction vectors are observed. It can be seen that the electrode acts as a field source and thus electric field directions are formed toward the direction of the reference electrode. In particular, it can be seen that electric field vectors are concentrated at the edges in the diagonal directions. The reason for this is that electric fields are concentrated in a place where the curvature of a metal surface is small, which is a common phenomenon that occurs in all general electrodes. Accordingly, in order to apply a high electric field to the flat portion that occupies most of the area of the electrode, a considerably high voltage needs to be applied. In this case, a problem arises in that an undesired excessively high electric field is formed locally at the corners and thus the electric field distribution becomes uneven.

Figure 3A:
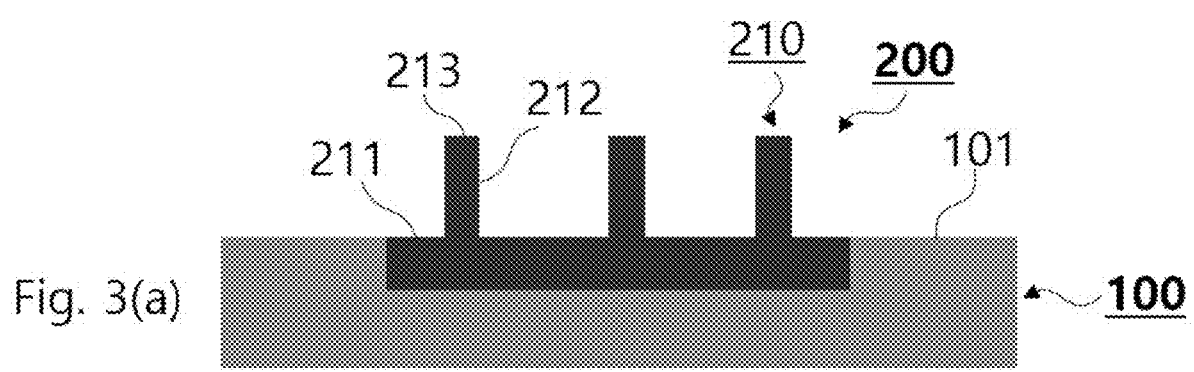
FIG. 3(a) is a shape sectional view of a plurality of protruding pillar electrodes.
Figure 3B:
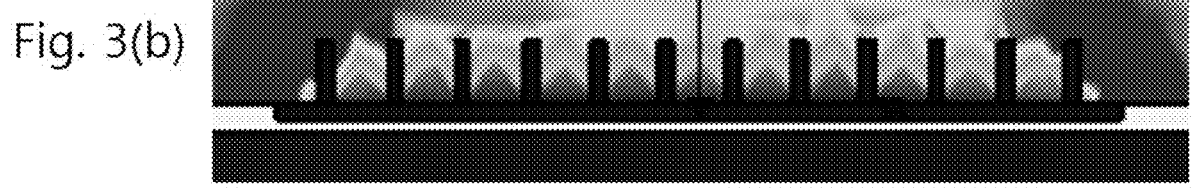
FIG. 3(b) shows the electric field distribution of the embodiment shown in FIG. 3(a)

FIG. 3(a) is a shape sectional view of a plurality of protruding pillar electrodes, and FIG. 3(b) shows the electric field distribution of the embodiment shown in FIG. 3(a).

FIG. 3 shows a shape section in which a surface is formed in a micro-pillar structure, not a conventional planar electrode structure, and the electric field distribution thereof.

In this embodiment, it can be seen that some fields are formed in the inside portion of the electrode unlike in the planar structure electrode of FIG. 2, and thus a more uniform field distribution is formed. However, it can be seen that the field is still not desirably formed in the center of the electrode.

A biosensor having a pillar-type electrode structure coated with a non-conductive material according to the present invention will be described in detail below. The biosensor according to the present invention may be operated to apply electrical stimulation to a living body, or may be operated to receive signals from the living body. In this specification, the following description will be given with a focus on a structure for applying electrical stimulation to a living body.

In the present invention, various thin film coating processes such as thermal evaporation, e-beam evaporation, CVD, and sputtering may be used as a method of coating microelectrodes, having a pillar structure, with a non-conductive material. In addition, in order to coat only a desired area, a desired shape may be implemented by various partial etching methods such as photolithography, chemical etching, Reactive Ion Etching (RIE), and Focused Ion Beam (FIB).

The biosensor according to the present invention includes: an electrode substrate 100; and an electrode structure 200 having a plurality of pillar electrodes 210 protruding on the substrate 100.

The present invention may have a first coating structure in which at least one or more of the plurality of pillar electrodes are coated with a non-conductive material 300 and at least a portion of the side surface 212 of each of the coated pillar electrodes is coated with the non-conductive material 300.

The present invention may have a second coating structure in which at least one of the top surface 101 of the substrate 100 and the bottom surfaces 211 of the at least one or more of the pillar electrodes 210 are coated with the non-conductive material 300.

In the present invention, the coating may be performed in at least one of the first and second coating structures. In other words, one of the first and second coating structures may be provided, or both of the first and second coating structures may be all provided.

In the present invention, there may be possible an embodiment in which the plurality of pillar electrodes 210 are provided such that the electrode heights He thereof are the same. In addition, there may be possible an embodiment in which the plurality of pillar electrodes 210 are provided such that the heights of the electrodes decrease toward the inside of the electrode structure 200 (see FIG. 10). Furthermore, there may be possible an embodiment in which the heights of the electrodes increase.

In the first coating structure according to the present invention, the coating height Hc of the side surfaces 212 of the pillar electrodes may be the same as the height He of the electrodes (see FIGS. 5, 6, and 7). In this embodiment, the top surfaces 213 of the pillar electrodes are not coated with a non-conductive material.

Meanwhile, in the first coating structure according to the present invention, there may be possible an embodiment in which the coating height Hc of the side surfaces 212 of the pillar electrodes is lower than the height He of the electrodes (see FIG. 8). In this embodiment, the top surfaces 213 of the pillar electrodes and the upper portions of the side surfaces 212 of the pillar electrodes are not coated with a non-conductive material.

In the first coating structure according to the present invention, there may be possible an embodiment in which the coating heights Hc of the side surfaces 212 of the pillar electrodes gradually decrease toward the inside of the plurality of pillar electrodes (see FIG. 11). In this embodiment, even when the electrode heights He of the pillar electrodes are the same, the upper areas of the side surfaces 212 that are not coated with a non-conductive material are further enlarged as the coating heights Hc decrease. Meanwhile, there may be possible an embodiment in which the coating heights Hc increase.

In the first coating structure according to the present invention, there may be possible an embodiment in which the pillar electrodes 210 to be coated are pillar electrodes disposed on the outermost sides of the electrode structure and the outer side surfaces 212 of the pillar electrodes disposed on the outermost sides of the electrode structure are coated with the non-conductive material 300 (see FIG. 9).

Furthermore, the electrode structure 200 according to the present invention may be provided such that a plurality of pillar electrode groups 210-Groups each including adjacent pillar electrodes are spaced apart from each other.

Meanwhile, the pillar electrodes according to the present invention may be provided in various shapes, e.g., polyhedral shapes such as a rectangular parallelepiped shape and a regular hexahedral shape, a cylindrical shape, and a conical shape.

In the present invention, there may be possible an embodiment in which a voltage is applied to predetermined ones 210_E of the plurality of pillar electrodes of the electrode structure 200 and the pillar electrodes 210_E to which the voltage is applied are spaced apart from each other.

In this embodiment, the bottom and side surfaces of the pillar electrodes 210_E to which the voltage is applied may be coated with the non-conductive material 300.

In the present invention, the electrode structure 200 may be provided such that a plurality of pillar electrode groups 210-Group each including adjacent pillar electrodes are spaced apart from each other and a voltage may be applied to pillar electrodes 210-E belonging to predetermined pillar electrode groups 210-Group.

In this embodiment, the bottom and side surfaces of the pillar electrodes 210_E to which the voltage is applied may be coated with the non-conductive material 300.

The features of the present invention will be described with reference to the drawings below.

Figure 4A:
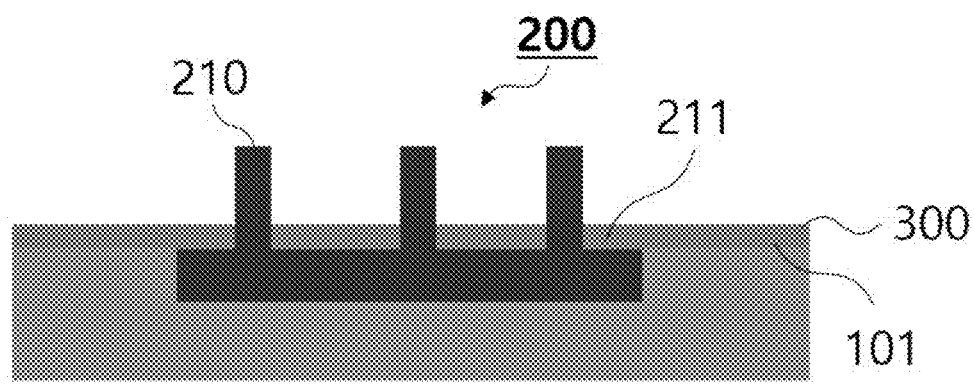
FIG. 4(a) shows an embodiment in which the top surface of a substrate and the bottom surfaces of pillar electrodes are coated with a non-conductive material.
Figure 4B:
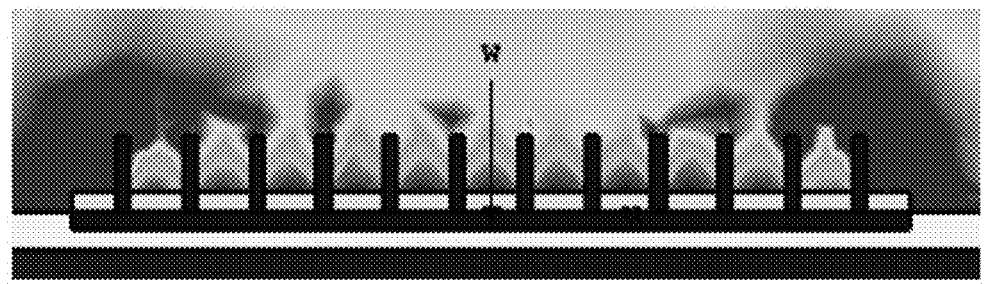
FIG. 4(b) shows the electric field distribution of the embodiment shown in FIG. 4(a)

FIG. 4(a) shows an embodiment in which the top surface of a substrate and the bottom surfaces of pillar electrodes are coated with a non-conductive material, and FIG. 4(b) shows the electric field distribution of the embodiment shown in FIG. 4(a).

FIG. 4 shows the shape of an electrode structure in which the bottom surfaces of pillar electrodes are coated with a non-conductive material and field distribution simulation results. It can be seen that some fields are formed even in the pillar electrodes located at the center of the electrode structure unlike in the embodiment of FIG. 3 to which the non-conductive material is not applied. The reason for this is that an animal or human body is composed of materials having electrical conductivity, and accordingly, the formation of fields in desired directions may be induced by coating one or more of the electrodes with a non-conductive material.

Figure 5A:
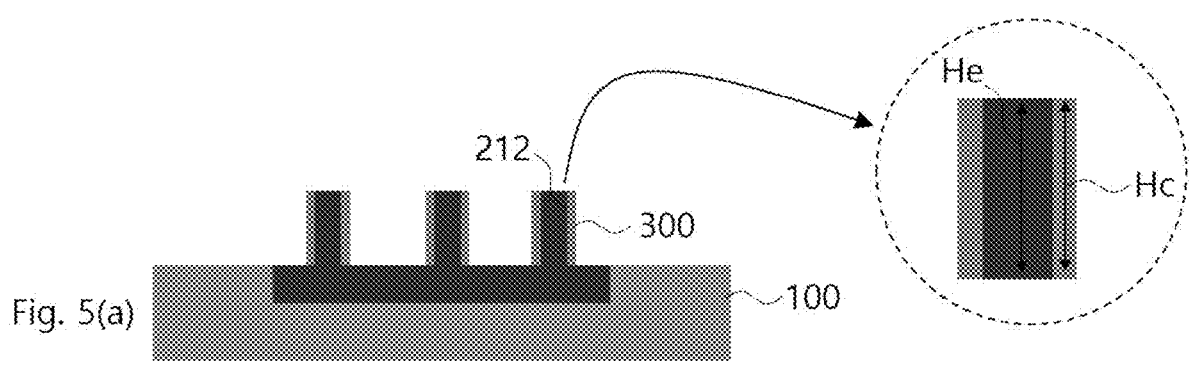
FIG. 5(a) shows an embodiment in which the side surfaces of pillar electrodes are coated with a non-conductive material.
Figure 5B:
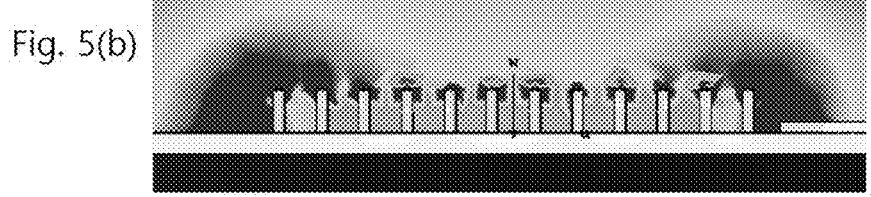
FIG. 5(b) shows the electric field distribution of the embodiment shown in FIG. 5(a)

FIG. 5(a) shows an embodiment in which the side surfaces of pillar electrodes are coated with a non-conductive material, and FIG. 5(b) shows the electric field distribution of the embodiment shown in FIG. 5(a).

FIG. 5 shows the results obtained by coating the surfaces of pillar electrodes, except the top surfaces thereof, with a non-conductive material. It can be seen that fields are formed at the ends of the pillar-type electrode structure like in the above-described results of the embodiment of FIG. 4. As described above, it can be seen that coating the pillar-type electrode structure with the non-conductive material plays an important role in the determination of the positions and directions at and in which fields are formed.

Figures 6A, 6B, 6C:
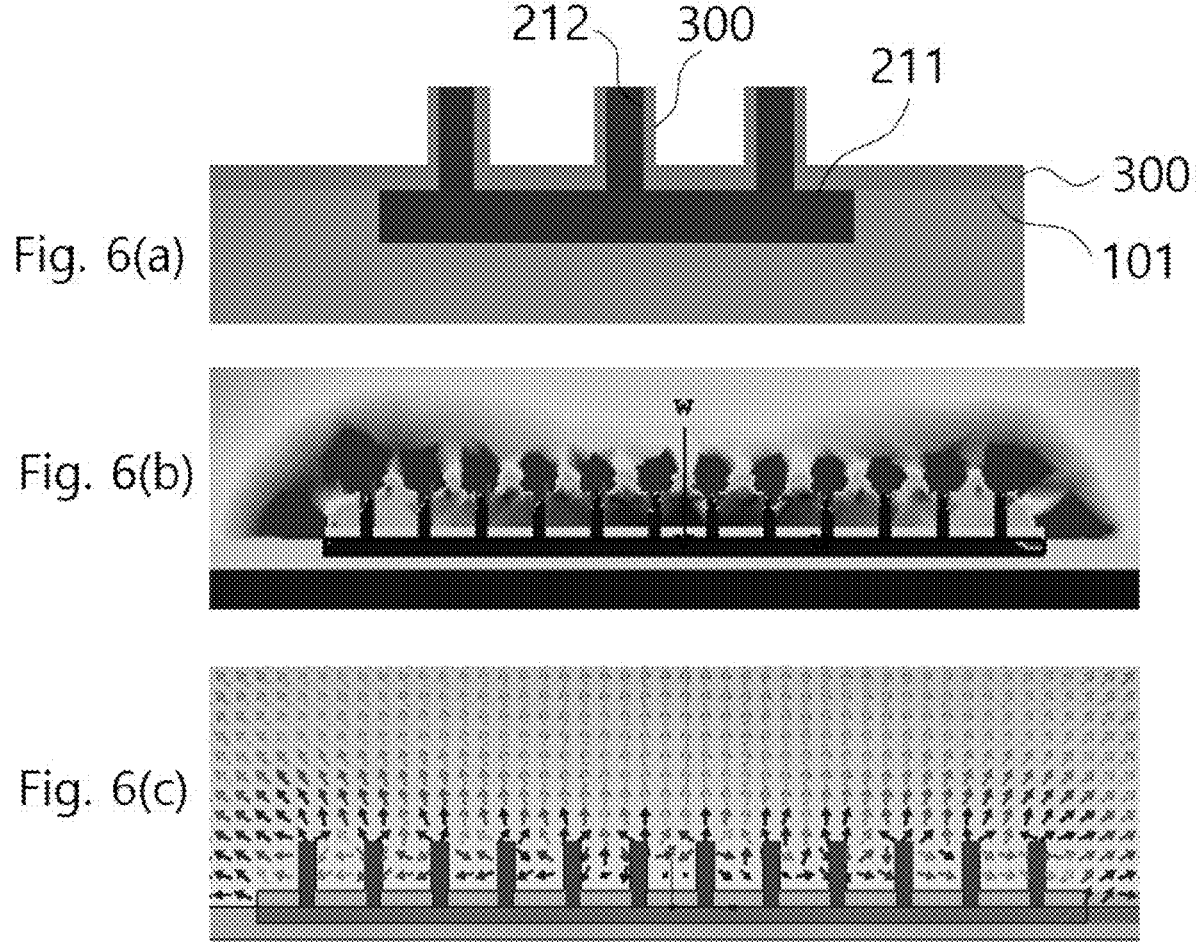
FIG. 6(a) shows an embodiment in which the top surface of a substrate and the bottom and side surfaces of pillar electrodes are coated with a non-conductive material.
FIG. 6(b) shows the electric field distribution of the embodiment shown in FIG. 6(a)
FIG. 6(c) shows the electric field directions of the embodiment shown in FIG. 6(a)

FIG. 6(a) shows an embodiment in which the top surface of a substrate and the bottom and side surfaces of pillar electrodes are coated with a non-conductive material, FIG. 6(b) shows the electric field distribution of the embodiment shown in FIG. 6(a), and FIG. 6(c) shows the electric field directions of the embodiment shown in FIG. 6(a).

FIG. 6 shows the results obtained by coating the side surfaces 212 of pillar electrodes, excluding the bottom and top surfaces 211 and 213 thereof, with a non-conductive material. As shown in FIG. 6, it can be seen that fields are evenly distributed over the overall electrode structure, and thus the fields may be concentrated on desired portions. Referring to the electric field direction vectors shown in FIG. 6(c), it can be seen that field vectors are strongly formed in directions upward from pillar electrodes, unlike in the film-type electrode embodiment of FIG. 2. Weak field vectors appear between the side surfaces of the pillar electrodes. As a result, it can be seen that interference and reinforcing effects appear between pillar electrodes in the pillar-type electrode structure, unlike in the film-type electrode structure, and thus electric fields are formed over a wide area, unlike in the film-type electrode structure. Accordingly, it may be possible to control fields by forming energy fields in desired regions in this manner.

Figure 7A:
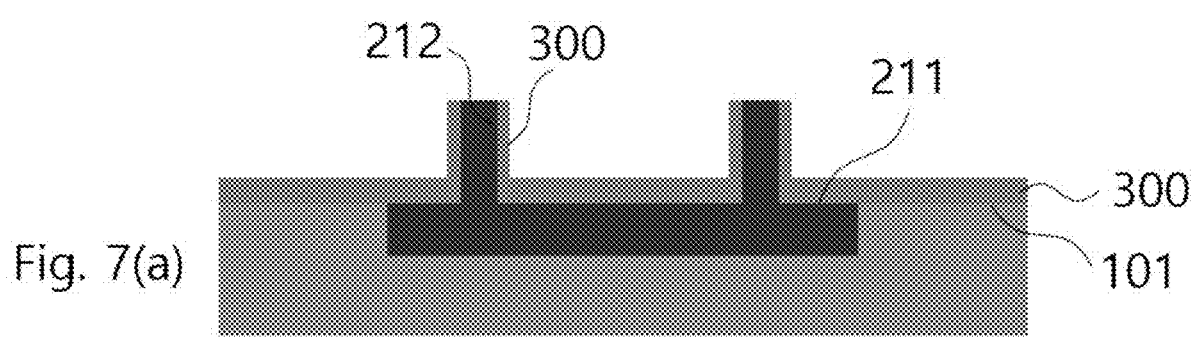
FIG. 7(a) shows an embodiment in which the interval between pillar electrodes is wider than that in the embodiment of FIG. 6(a)
Figure 7B:
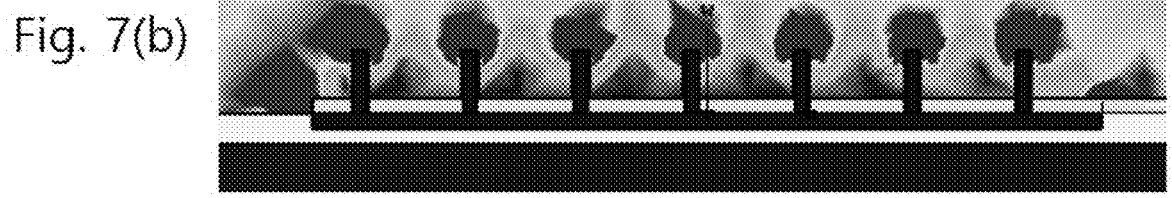
FIG. 7(b) shows the electric field distribution of the embodiment shown in FIG. 7(a)

FIG. 7(a) shows an embodiment in which the interval between pillar electrodes is wider than that in the embodiment of FIG. 6(a), and FIG. 7(b) shows the electric field distribution of the embodiment shown in FIG. 7(a).

In FIG. 7, there is shown a structure that is formed the same as in FIG. 6 but the interval between pillar electrodes is increased. In this embodiment, it can also be seen that energy fields are desirably formed on the top surfaces of pillar electrodes. Accordingly, it may be possible to utilize the interval between or shape of the pillar electrodes as a variable for the control of energy fields.

FIG. 8(a) shows an embodiment in which the top surface of a substrate and the bottom and side surfaces of pillar electrodes are coated with a non-conductive material and the coating height Hc of the side surfaces of the pillar electrodes is lower than the height He of the electrodes, and FIG. 8(b) shows the electric field distribution of the embodiment shown in FIG. 8(a).

In the embodiment of FIG. 8, the coated areas of the side surfaces 212 of the pillar electrodes are partially exposed in the structure of the embodiment shown in FIG. 6. Through this, it can be seen that the shape in which fields are formed in a pillar-type electrode structure is changed. As described above, it can be seen that the area which is not coated with the non-conductive material may also be a variable for the control of energy fields.

Figure 9A:
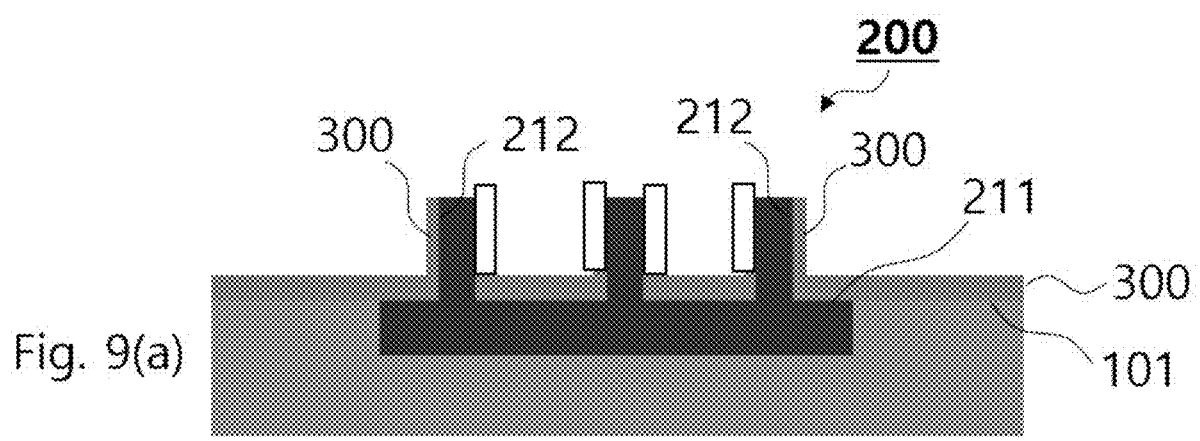
FIG. 9(a) shows an embodiment in which the top surface of a substrate and the bottom and side surfaces of pillar electrodes are coated with a non-conductive material and the outer side surfaces of pillar electrodes disposed on the outermost sides are coated with a non-conductive material.
Figure 9B:
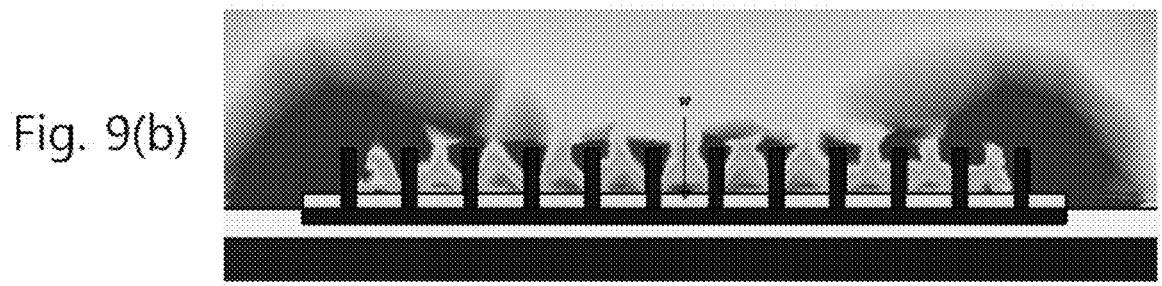
FIG. 9(b) shows the electric field distribution of the embodiment shown in FIG. 9(a)

FIG. 9(a) shows an embodiment in which the top surface of a substrate and the bottom and side surfaces of pillar electrodes are coated with a non-conductive material and the outer side surfaces 212 of pillar electrodes disposed on the outermost sides are coated with a non-conductive material, and FIG. 9(b) shows the electric field distribution of the embodiment shown in FIG. 9(a).

In the embodiment of FIG. 9, only one of the side surfaces 212 of each of the pillar electrodes is coated with a non-conductive material. It can be seen that the energy field distribution can be changed through the control of coated areas.

The electrode structure 200 according to the present invention may be provided such that a plurality of pillar electrode groups 210-Groups each including adjacent pillar electrodes are spaced apart from each other.

Figures 10A, 10B:
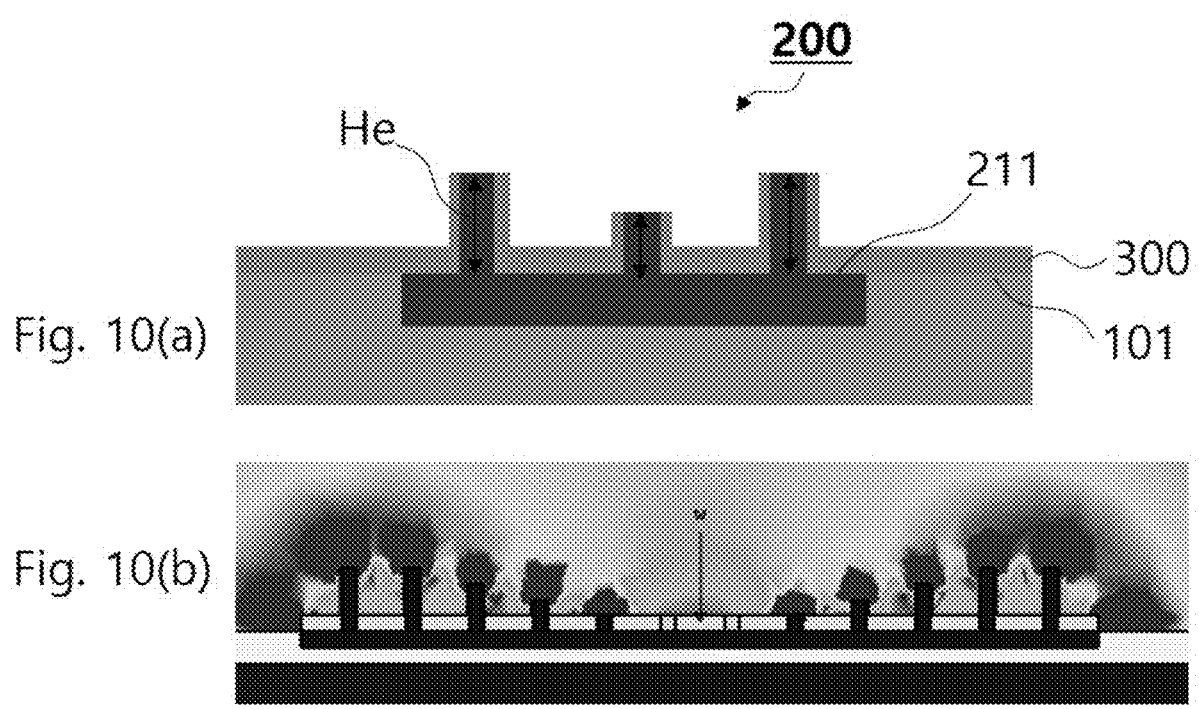
FIG. 10(a) shows an embodiment in which the top surface of a substrate and the bottom and side surfaces of pillar electrodes are coated with a non-conductive material and the heights of the pillar electrodes decrease toward the inside of a pillar-type electrode structure.
FIG. 10(b) shows the electric field distribution of the embodiment shown in FIG. 10(a)

FIG. 10(a) shows an embodiment in which the top surface of a substrate and the bottom and side surfaces of pillar electrodes are coated with a non-conductive material and the heights He of the pillar electrodes decrease toward the inside of a pillar-type electrode structure, and FIG. 10(b) shows the electric field distribution of the embodiment shown in FIG. 10(a).

In the embodiment of FIG. 10, the bottom and side surfaces of the pillar electrodes are coated with the non-conductive material and the heights of pillar electrodes are different in a partial section, unlike in the embodiment of FIG. 6. It can be seen that the electric field distribution may be changed and adjusted according to the height He of the electrodes.

Figure 11A:
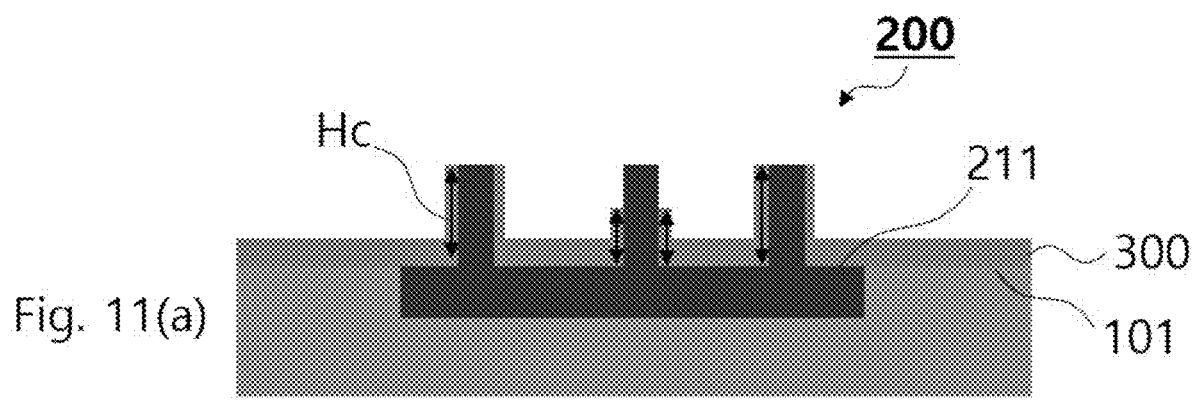
FIG. 11(a) shows an embodiment in which the top surface of a substrate and the bottom and side surfaces of pillar electrodes are coated with a non-conductive material and the coating heights of the sides of the pillar electrodes gradually decrease toward the inside of a pillar-type electrode structure.
Figure 11B:
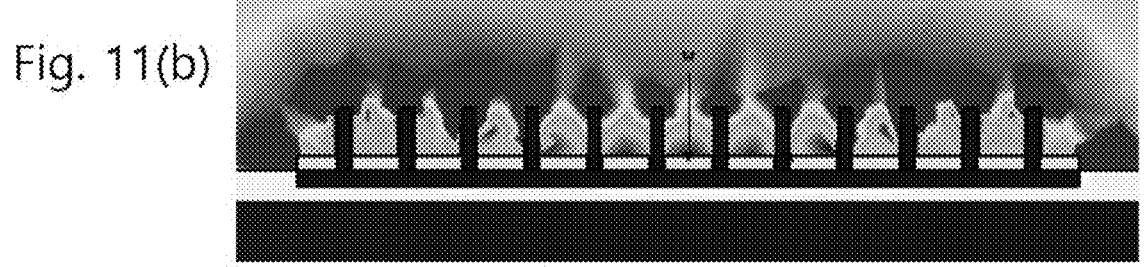
FIG. 11(b) shows the electric field distribution of the embodiment shown in FIG. 11(a)

FIG. 11(a) shows an embodiment in which the top surface of a substrate and the bottom and side surfaces of pillar electrodes are coated with a non-conductive material and the coating heights Hc of the sides of the pillar electrodes gradually decrease toward the inside of a pillar-type electrode structure, and FIG. 11(b) shows the electric field distribution of the embodiment shown in FIG. 11(a).

In the embodiment of FIG. 11, the heights of the pillar electrodes are the same, but the coating heights Hc of the non-conductive material formed on the respective pillar electrodes are different. As shown in the drawing, it can be seen that an even electric field distribution may be obtained over a wider area by making the coating heights Hc of the non-conductive material different even for the same electrode height He than the embodiment of FIG. 6.

Figure 12A:
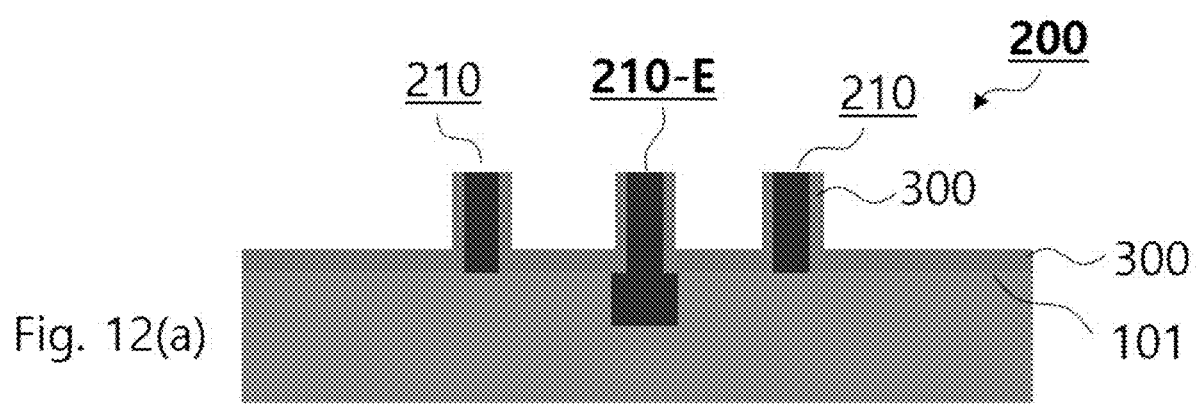
FIG. 12(a) shows an embodiment in which the top surface of a substrate and the bottom and side surfaces of pillar electrodes are coated with a non-conductive material, electricity is supplied only to predetermined ones of the plurality of pillar electrodes, and the pillar electrodes to which electricity is supplied are spaced apart from each other.
Figure 12B:
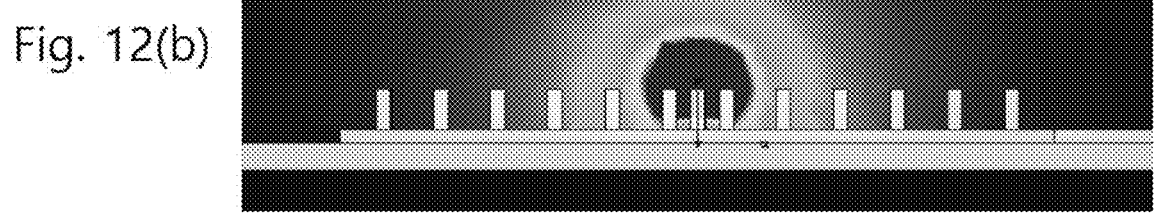
FIG. 12(b) shows the electric field distribution of the embodiment shown in FIG. 12(a)

FIG. 12(a) shows an embodiment in which the top surface of a substrate and the bottom and side surfaces of pillar electrodes are coated with a non-conductive material, electricity is supplied only to predetermined ones 210_E of the plurality of pillar electrodes, and the pillar electrodes 210_E to which electricity is supplied are spaced apart from each other, and FIG. 12(b) shows the electric field distribution of the embodiment shown in FIG. 12(a).

In the embodiment of FIG. 12, there is formed a pillar-type electrode structure in which the bottom and side surfaces of the pillar electrodes are coated with the non-conductive material, as in the embodiment of FIG. 6. There are shown a sectional view and an electric field distribution in the case where a voltage is applied to only one or more of the pillar electrodes (one pillar electrode in the case of FIG. 12(a)). It can be seen that since electric energy is fed only to one pillar electrode, unlike in the embodiment of FIG. 6, an electric field is formed only in a portion to which a voltage is applied. Accordingly, it can be seen that the electric field distribution may be adjusted according to the pillar electrode to which the voltage is applied.

Furthermore, a more important point is that electric fields may be concentrated around the pillar electrode to which the voltage is applied. Through this, it may be possible not only to control the electric field distribution but also to significantly increase the intensity of an electric field.

In the case of the embodiment of FIG. 6, the intensity of the electric fields formed around the pillar electrodes is about 4,000 V/m. In contrast, in the case of the embodiment of FIG. 12 in which a voltage is applied only to one pillar electrode, it can be seen that the intensity of the electric field increases to about 40,000 V/m by about 10 times. Accordingly, energy may be concentrated by controlling the number, placement, and intensity of pillar electrodes to which a voltage is applied.

Figure 13A:
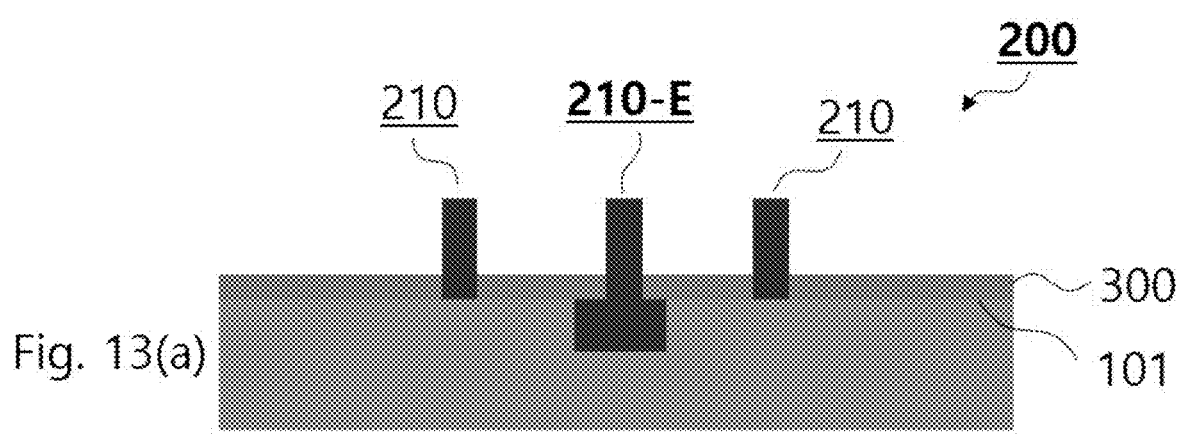
FIG. 13(a) shows an embodiment in which the top surface of a substrate and the bottom surfaces of pillar electrodes are coated with a non-conductive material, electricity is supplied only to predetermined ones of the plurality of pillar electrodes, and the pillar electrodes to which electricity is supplied are spaced apart from each other.
Figure 13B:
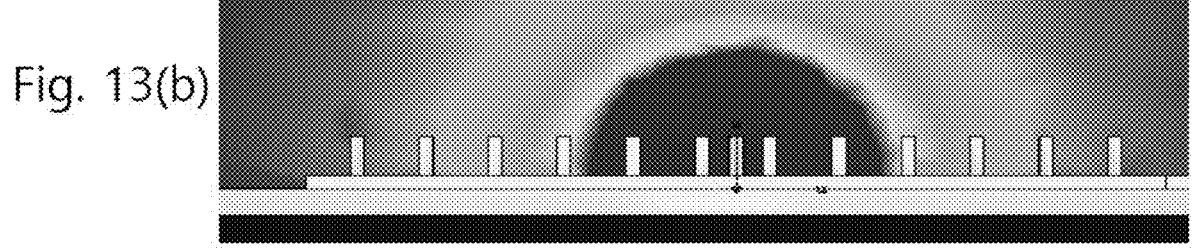
FIG. 13(b) shows the electric field distribution of the embodiment shown in FIG. 13(a)

FIG. 13(a) shows an embodiment in which the top surface of a substrate and the bottom surfaces of pillar electrodes are coated with a non-conductive material, electricity is supplied only to predetermined ones 210_E of the plurality of pillar electrodes, and the pillar electrodes 210_E to which electricity is supplied are spaced apart from each other, and FIG. 13(b) shows the electric field distribution of the embodiment shown in FIG. 13(a).

In the embodiment of FIG. 13, there are shown a sectional view and an electric field distribution in the case where a pillar-type electrode structure in which the bottom surfaces of the pillar electrodes are coated with the non-conductive material is formed, as in the embodiment of FIG. 4, and a voltage is applied only to one of the plurality of pillar electrodes, as in the embodiment of FIG. 12. In this case, it can be seen that electric field energy is concentrated and distributed only around the electrode to which the voltage is applied.

Furthermore, in the embodiment of FIG. 4, the pillar electrode located at the center exhibits a lower electric field distribution than the pillar electrodes located at the corners (the outer sides), and the value thereof is about 700 V/m.

However, in the case of the embodiment of FIG. 13, an electric field of about 20,000 V/m is formed around the pillar electrode to which the voltage is applied, and thus the electric field is concentrated about 30 times at the center.

FIG. 14(a) shows an embodiment in which an electrode structure 200 is provided such that a plurality of pillar electrode groups 210-Groups each including adjacent pillar electrodes are spaced apart from each other and electricity is supplied to pillar electrodes 210-E belonging to predetermined pillar electrode groups 210-Group. FIG. 14(b) shows the electric field distribution of the embodiment shown in FIG. 14(a). FIG. 14(c) shows a state in which the plurality of pillar electrode groups 210-Groups are provided to be spaced apart from each other.

In the embodiment of FIG. 14, there are shown a sectional view and electric field distribution of the embodiment in which there is formed the electrode structure in which the bottom and side surfaces of the pillar electrodes are coated with the non-conductive material, as in the embodiment of FIG. 12, and a voltage is applied to each of the pillar electrodes.

As shown in the drawing, it can be seen that electric fields are desirably formed around the pillar electrodes to which the voltage is applied, and thus an electric field distribution may be formed at desired locations by adjusting the positions of the pillar electrodes to which the voltage is applied individually.

As described above, according to the present invention, it can be seen that energy can be dispersed/concentrated by adjusting an electric field to a desired shape by controlling the coated area of a non-conductive material and a target for the application of a voltage.

The biosensor having a pillar-type electrode structure coated with a non-conductive material according to the present invention has the following effects:

First, there is achieved the effect of proposing a structure that concentrates energy formed between microelectrodes.

Second, there is achieved the effect of controlling the size and area of concentrated energy by forming microelectrodes in a pillar structure and changing the pillar structure and shape.

Third, there is achieved the effect of controlling the size and area of concentrated energy by coating microelectrodes and a substrate with a non-conductive material.

Fourth, there is achieved the effect of controlling the size and area of concentrated energy by selecting one or more electrodes to which a voltage is applied.

The effects of the present invention are not limited to those mentioned above, and other effects that are not mentioned will be clearly understood by those skilled in the art from the following description.

The embodiments described in the present specification and the accompanying drawings are merely illustrative of some of the technical spirit included in the present invention. Therefore, it is obvious that the embodiments disclosed in the present specification are not intended to limit the technical spirit of the present disclosure but is intended to describe the technical spirit, so that the scope of the technical spirit of the present invention is not limited by these embodiments. Modifications and specific embodiments that can be easily inferred by those skilled in the art without departing from the scope of the technical spirit included in the specification and drawings of the present invention should be interpreted as being included in the scope of the present invention.

What is claimed is:

1. A biosensor capable of receiving bioelectric stimulation or bio-signals, the biosensor having a pillar-type electrode structure coated with a non-conductive material, the biosensor comprising:
an electrode substrate; and
an electrode structure having a plurality of pillar electrodes protruding on the substrate;
wherein at least one or more of the plurality of pillar electrodes are coated with the non-conductive material and at least a portion of a side surface of each of the coated pillar electrodes is coated with the non-conductive material,
wherein the plurality of pillar electrodes are spaced apart from each other with an empty space therebetween,
wherein a height of the plurality of pillar electrodes protruding in the empty space is greater than a height of the plurality of pillar electrodes between the electrode substrate and the empty space,
wherein a coating height on the side surfaces of at least one of the plurality of pillar electrodes is a same as the electrode height, and
wherein a coating height on the side surfaces of at least one of the plurality of pillar electrodes is lower than the electrode height.

2. The biosensor of claim 1, wherein the plurality of pillar electrodes have a same electrode height.

3. The biosensor of claim 2, wherein coating heights on the side surfaces of the pillar electrodes gradually decrease or increase toward an inside of the plurality of pillar electrodes.

4. The biosensor of claim 2, wherein the pillar electrodes to be coated are pillar electrodes disposed on outermost sides of the electrode structure and outer side surfaces of the pillar electrodes disposed on the outermost sides of the electrode structure are coated with the non-conductive material.

5. The biosensor of claim 2, wherein the electrode structure is provided such that a plurality of pillar electrode groups each including adjacent pillar electrodes are spaced apart from each other.

6. The biosensor of claim 1, wherein the plurality of pillar electrodes are provided such that electrode heights thereof decrease or increase toward an inside of the electrode structure.

7. The biosensor of claim 6, wherein coating heights on the side surfaces of the pillar electrodes gradually decrease or increase toward an inside of the plurality of pillar electrodes.

8. The biosensor of claim 6, wherein the pillar electrodes to be coated are pillar electrodes disposed on outermost sides of the electrode structure and outer side surfaces of the pillar electrodes disposed on the outermost sides of the electrode structure are coated with the non-conductive material.

9. The biosensor of claim 6, wherein the electrode structure is provided such that a plurality of pillar electrode groups each including adjacent pillar electrodes are spaced apart from each other.

10. The biosensor of claim 1, wherein a voltage is applied to predetermined one or more of the plurality of pillar electrodes of the electrode structure.

11. The biosensor of claim 10, wherein the pillar electrodes to which the voltage is applied are spaced apart from each other.

12. The biosensor of claim 10, wherein at least one of bottom and side surfaces of each of the pillar electrodes to which the voltage is applied is coated with the non-conductive material.

13. The biosensor of claim 1, wherein:
the electrode structure is provided such that a plurality of pillar electrode groups each including adjacent pillar electrodes are spaced apart from each other; and
a voltage is applied to pillar electrodes belonging to predetermined one or more of the pillar electrode groups.

14. The biosensor of claim 13, wherein bottom and side surfaces of each of the pillar electrodes to which the voltage is applied are coated with the non-conductive material.

* * * * *